United States Patent [19]
Yamada et al.

[11] Patent Number: 6,015,696
[45] Date of Patent: Jan. 18, 2000

[54] MYCOBACTERIAL SECRETORY EXPRESSION VECTORS AND TRANSFORMANTS

[75] Inventors: Takeshi Yamada, Nagasaki-ken; Kazuhiro Matsuo, Kaswaski; Ryuji Yamaguchi, Kawasaki; Akihiro Yamazaki, Kawasaki, all of Japan

[73] Assignees: Ajinomoto, Co., Inc., Tokyo; Takeshi Yamada, Nagasaki-ken, both of Japan

[21] Appl. No.: 08/193,899

[22] Filed: Feb. 9, 1994

Related U.S. Application Data

[63] Continuation of application No. 07/531,448, May 31, 1990, abandoned.

[30] Foreign Application Priority Data

May 31, 1989 [JP] Japan ..................................... 1-135855
Mar. 16, 1990 [JP] Japan ..................................... 2-64310

[51] Int. Cl.$^7$ ............................ C12N 1/21; C12N 15/74; C12P 21/00; C12P 21/02
[52] U.S. Cl. .................... 435/69.8; 424/200.1; 435/69.1; 435/69.3; 435/69.7; 435/252.3
[58] Field of Search .................................. 435/69.1, 7.2, 435/7.3, 320.1, 71.3, 543, 252.3, 69.3, 69.7, 69.8, 132.3; 424/93 A, 89, 200.1; 514/2

[56] References Cited

U.S. PATENT DOCUMENTS

| | | | |
|---|---|---|---|
| 4,880,626 | 11/1989 | McMichael | 424/184.1 |
| 4,965,197 | 10/1990 | Liebl et al. | 435/69.8 |
| 5,001,230 | 3/1991 | Brown et al. | 536/23.5 |
| 5,019,384 | 5/1991 | Gefter et al. | 424/184.1 |
| 5,279,960 | 1/1994 | Anderson et al. | 435/243 |
| 5,294,441 | 3/1994 | Curtiss, III | 424/200.1 |
| 5,504,005 | 4/1996 | Bloom et al. | 435/472 |
| 5,591,632 | 1/1997 | O'Donnell et al. | 435/252.3 |
| 5,776,365 | 7/1998 | O'Donnell et al. | 424/200.1 |
| 5,830,475 | 11/1998 | Aldovini et al. | 424/200.1 |

FOREIGN PATENT DOCUMENTS

WO/8806626 12/1989 WIPO.
WO/9000594 2/1990 WIPO.

OTHER PUBLICATIONS

Jacobs, Jr. et al., Nature 327:532–534 (1987).
Aldovini et al., Nature 351:479–482 (1991).
Microbiology, Bernard D. Davis et al., eds. Hagerstown: Harper & Row, Publishers, 1980, p. 294.
Cohen et al., JAMA 280(1):87–88 (1998).
Davis et al, J. Gen. Microbiol., vol. 56 (1969), pp. 195–214: "Numerical Taxonomy of Some Named Coryneform Bacteria".
Yamada et al, J. Gen. Appl. Microbiol., vol. 18 (1972), pp. 417–431: "Taxonomic Studies of Coryneform Bacteria v. Classification of Coryneform Bacteria".
Veldkamp, Ann. Rev. Microbiol., vol. 24 (1970), pp. 209–240: "Saprophytic Coryneform Bacteria".
Proceedings of the National Academy of Science, USA, vol. 85, Sep. 1988, pp. 6987–6991; S.B. Snapper et al.: "Lysogony and transformation in mycobacteria: Stable expression of foreign genes".
Matsuo et al., J. of Bacteriology 170(9):3847–3854 (1988).
Ghrayeb, et al., DNA, vol. 5, No. 2, (1986) p. 93–99.

*Primary Examiner*—Johnny F. Railey, II
*Attorney, Agent, or Firm*—Oblon, Spivak, McClelland, Maier & Neustadt, P.C.

[57] ABSTRACT

A secretory vector expressed in mycobacteria comprising a promoter, a signal sequence having ligated therewith a DNA nucleotide sequence encoding heterologous polypeptide and replicator region capable of replication in mycobacteria is disclosed. A transformant that has been transformed with the secretory vector, as well as a vaccine comprising the transformant is provided.

9 Claims, 6 Drawing Sheets

```
                                GTTAACTATTCTTTGTACCGCTCCCCGCC

TGCCGCCTTCTGCCCTGCTCCGGGTGCATAGCACCCGTTTGCGCTCCGGATTATCCGGGC

CGCAACGGGGCAACGGGGGAAGCGGTGGAGTCCGTCGCCGACTCGCATAGCACCGTTGCT

GTGTTGGCGGGGGTAACCGATATCGAAATGGAATGACTTCGCGTCCCGATCGACATTTGC
                                                      -35
CCTACTCACACGGTAAGTTCTGCCGGGAGCACGCGAGCACATACGGACAAGGGGCAGGGT
          -10                                      SD
     10        20        30        40        50        60
ATGACAGACGTGAGCGGGAAGATTCGGGCGTGGGGCCGACGCCTTCTGGTCGGCGCGGCC
MetThrAspValSerGlyLysIleArgAlaTrpGlyArgArgLeuLeuValGlyAlaAla    SIGNAL
                                                               PEPTIDE
     70        80        90       100       110       120
GCTGCTGCGGCCCTTCCTGGCCTGGTCGGACTCGCCGGCGGAGCGGCGACCGCGGGAGCG
AlaAlaAlaAlaLeuProGlyLeuValGlyLeuAlaGlyGlyAlaAlaThrAlaGlyAla 130       140       150       160       170       180
TTCTCCCGTCCCGGCCTGCCGGTGGAGTACCTCCAGGTGCCGTCGGCTGCGATGGGTCGC
PheSerArgProGlyLeuProValGluTyrLeuGlnValProSerAlaAlaMetGlyArg 190       200       210       220       230       240
AGTATCAAGGTTCAATTCCAAAGTGGCGGGGACAACTCGCCGGCGGTGTACCTGCTCGAC
SerIleLysValGlnPheGlnSerGlyGlyAspAsnSerProAlaValTyrLeuLeuAsp 250       260       270       280       290       300
GGTCTCCGCGCTCAAGACGACTACAACGGCTGGGACATCAACACCCCGGCCTTCGAGTGG
GlyLeuArgAlaGlnAspAspTyrAsnGlyTrpAspIleAsnThrProAlaPheGluTrp 310       320       330       340       350       360
TACTACCAATCGGGCCTGTCGGTCATCATGCCGGTCGGCGGACAGTCCAGTTTCTACAGT
TyrTyrGlnSerGlyLeuSerValIleMetProValGlyGlyGlnSerSerPheTyrSer 370       380       390       400       410       420
GACTGGTACAGCCCGGCCTGCGGCAAGGCCGGCTGCACGACCTACAAGTGGGAGACCTTC
AspTrpTyrSerProAlaCysGlyLysAlaGlyCysThrThrTyrLysTrpGluThrPhe
```

*FIG. 1A*

```
         430       440       450       460       470       480
CTGACCAGCGAGCTGCCGCAATGGCTGTCCGCGAACCGGAGTGTCAAGCCCACCGGAAGC
LeuThrSerGluLeuProGlnTrpLeuSerAlaAsnArgSerValLysProThrGlySer 490       500       510       520       530       540
GCCGCGGTCGGCATCTCGATGGCCGGCTCGTCGGCCCTGATCCTGTCCGTCTACCACCCG
AlaAlaValGlyIleSerMetAlaGlySerSerAlaLeuIleLeuSerValTyrHisPro 550       560       570       580       590       600
CAGCAGTTCATCTACGCGGGTTCGTTGTCGGCCCTGATGGACCCCTCCCAGGGGATCGGG
GlnGlnPheIleTyrAlaGlySerLeuSerAlaLeuMetAspProSerGlnGlyMetGly 610       620       630       640       650       660
CCGTCTCTGATCGGCTTGGCGATGGGTGACGCCGGTGGTTACAAGGCCTCGGACATGTGG
ProSerLeuIleGlyLeuAlaMetGlyAspAlaGlyGlyTyrLysAlaSerAspMetTrp 670       680       690       700       710       720
GGACCCTCGAGTGACCCAGCCTGGCAGCGTAACGACCCGTCGCTGCACATTCCGGAGCTG
GlyProSerSerAspProAlaTrpGlnArgAsnAspProSerLeuHisIleProGluLeu 730       740       750       760       770       780
GTCGCCAACAACACCCGCCTGTGGATCTACTGCGGCAACGGCACCCCGTCCGAGTTGGGC
ValAlaAsnAsnThrArgLeuTrpIleTyrCysGlyAsnGlyThrProSerGluLeuGly 790       800       810       820       830       840
GGTGCCAATGTTCCGGCCGAATTCCTGGAGAACTTCGTTCGCAGCAGCAACCTGAAATTC
GlyAlaAsnValProAlaGluPheLeuGluAsnPheValArgSerSerAsnLeuLysPhe 850       860       870       880       890       900
CAGGACGCCTACAACGCCGCGGGCGGCCACAACGCCGTGTTCAATTTGGACGCCAACGGA
GlnAspAlaTyrAsnAlaAlaGlyGlyHisAsnAlaValPheAsnLeuAspAlaAsnGly 910       920       930       940       950       960
ACGCACAGCTGGGAGTACTGGGGCGCGCAGCTCAACGCCATGAAGGGTGACCTGCAGGCC
ThrHisSerTrpGluTyrTrpGlyAlaGlnLeuAsnAlaMetLysGlyAspLeuGlnAla 970       980
AGCCTGGGCGCCCGCTGATCGCGCAACGGTTGCCGCTACTGGGCTTGACGGCAAGACGCC
SerLeuGlyAlaArg***

GTCAAGCCAGTAGTGTGTTCGGCACCTTGAACGCTGGTCCGCCATGTTCAACGAGCCGGT
CTACCTGCCCGCACCGAACAAGCTGGTGACATCGACCCATGCGGTGC
```

MYCOBACTERIAL SECRETORY EXPRESSION VECTORS AND TRANSFORMANTS

The present application is a continuation of application Ser. No. 07/531,448, filed May 31, 1990, abandoned.

BACKGROUND OF THE INVENTION

1. Field of the Invention

The present invention relates to a secretory expression vector capable of extracellularly secreting heterologous polypeptides in mycobacteria.

2. Discussion of the Background

BCG, which is one of the mycobacteria, is an attenuated strain obtained by subculturing bovine tubercle bacillus selected among tubercle bacilli capable of proliferating even in macrophage in an artificial medium over 20 years. BCG is characterized in that it is the only live vaccine which is currently being used as a bacterial vaccine in human. It has extremely weak toxicity, and it has a strong non-specific cellular immunity potentiating effect (adjuvant activity) not only in tuberculous infection but also in various other infections. It is also relatively inexpensive. Accordingly, if BCG can be made to secrete antigenic polypeptides of various pathogenic bacteria or viruses by using genetic engineering techniques, it would be possible to develop a live vaccine of recombinant BCG having the following advantages:

(1) high safety;

(2) long-lasting activity;

(3) vaccine activity induced by the strong adjuvant activity of BCG per se;

(4) low costs;

At present, the vaccinia virus has been widely used as a vector in the study of recombinant live vaccines. However, the vaccinia virus has drawbacks because there is the danger that a virulent revertant might appear. For example, encephalitis might be caused when inoculated in humans. Thus, the vaccinia virus is far from practical use and attention has now been directed to BCG, which is safe and can provide a strong adjuvant effect.

On the other hand, no report of the expression of exogenous genes in mycobacteria by genetic engineering has been made since the transformation system itself has not been established yet. However, this goal has recently become possible because the transformation system by electroporation has been established. (Proc. Natl. Acad. Sci. U.S.A., 85, 6987 (1988)). In this system, a shuttle vector of *Escherichia coli*-mycobacteria fused with vector pIJ666 of *Escherichia coli* and plasmid pAL5000 derived from *Mycobacterium fortuitum* (FEMS Microbiol. Lett., 30, 221 (1985).) is introduced into mycobacteria by electroporation. Using this system, it was shown that a kanamycin-resistance gene (kanamycin phosphotransferase gene), derived from *Escherichia coli*, can be expressed in mycobacteria.

However, no systems capable of secreting exogenous polypeptides from mycobacteria such as proteins of the AIDS virus are available in the prior art. Such a system would provide a more effective vaccine.

SUMMARY OF THE INVENTION

An object of the present invention is to provide a secretory vector capable of secreting heterologous polypeptide from mycobacteria, especially from BCG.

Another object of this invention is to provide a transformant that has been transformed with the secretory vector.

Another object is to provide a vaccine comprising the transformant.

The inventors have now discovered that these objects and other objects, which will be apparent from the description of the invention set forth below, are satisfied with a vector expressed in mycobacteria comprising a promoter, a signal sequence having ligated therewith a DNA nucleotide sequence encoding a heterologous polypeptide, and a replicator region capable of replication in mycobacteria.

DETAILED DESCRIPTION OF THE PREFERRED EMBODIMENTS

The present invention relates to a secretory expression vector capable of extracellularly secreting heterologous polypeptides in mycobacteria represented by *Mycobacterium bovis* BCG (hereinafter simply referred to as BCG) and transformants transformed with the vectors.

The secretion of a heterologous polypeptide from mycobacteria has been achieved using a vector comprising a promoter, a signal sequence having ligated therewith a DNA sequence encoding heterologous polypeptide, and a replicator region capable of replication in mycobacteria, and a transformant transformed with the vector.

The promoter sequence incorporated into the vector of the present invention essentially requires a sequence of about −35 and −10 base pairs from the transcriptional initiation site which is recognized by RNA polymerase of mycobacteria. A consensus sequence in these regions has not yet been determined in mycobacteria, but a variety of sequences similar to the consensus sequences of *Escherichia coli* (TTGACA, −35 region or TATAAT, −10 region) have been reported also on mycobacteria. However, a promoter of mycobacteria having a sequence quite different from such a consensus sequence is present. It is therefore desirable to use the sequence of the −35 and −10 regions of a gene which is actually highly expressed in mycobacteria as it is, or to use synthetic DNA obtained by artificial synthesis of the sequence.

The DNA sequence encoding signal peptide is a sequence coding for a peptide composed of 20 to 40 amino acid residues. This region is required for extracellular secretion of a protein through the cytoplasmic membrane. The structural characteristics of the signal peptide lie in that the signal peptide contains Met, corresponding to the initiation codon ATG at the $NH_2$-terminal. Two to three basic amino acids (Lys, Arg, etc.) are present around the $NH_2$-terminal. Fifteen to twenty-five hydrophobic amino acids follow the basic amino acids, and a cleavage site of the signal peptide is composed of amino acid residues having a short side chain such as Ala, Gly and the like. These structural characteristics are common to various species of organism but their amino acid sequences and nucleotide sequences of signal peptide are subtly different. Therefore, it is desirable to use a signal sequence of a protein actually extracellularly secreted from mycobacteria in large quantities as it is, or to use synthetic DNA obtained by artificially synthesizing such a signal sequence.

The DNA fragment containing the promoter sequence and the DNA sequence encoding the signal peptide described above can be excised from the gene of a secretory protein, α antigen, which has already been cloned from chromosomal DNA of BCG by the present inventors, (J. Bacteriol., 170, 3847 (1988)), MPB64 protein, (Infect. Immun., 57, 283 (1989)), MPB70 protein, (FEMS Microbiol. Lett., 58, 273 (1989)), or α antigen gene cloned from chromosomal DNA of *Mycobacterium kansasii* (Infect. Immun., 58, 550 (1990)).

An example of the preparation of the DNA fragment is illustratively shown with respect to the cloning of the *Mycobacterium kansasii*-derived α antigen gene. Firstly, chromosomal DNA of *Mycobacterium kansasii* can be prepared in a manner similar to the method of Suzuki et al. (J. Bacteriol., 169, 839 (1987)). This chromosomal DNA is digested with various restriction enzymes then fractionated by agarose gel electrophoresis followed by the Southern hybridization using the α antigen gene fragment or a synthetic oligonucleotide having a complementary sequence to the nucleotide sequence deduced from a partial amino acid sequence of α antigen as a probe (J. Mol. Biol., 98, 503 (1975)). In this way, the desired DNA fragment is detected. Then the DNA fragment fractionated by electrophoresis is extracted from the gel, introduced into a cloning vector (e.g., plasmid pUC18, p BR322, etc.) and introduced into host cells (e.g., *Escherichia coli* JM109 strain, HB101 strain, etc.) by the method of Hanahan (J. Mol. Biol., 166, 557 (1983)) or by the competent cell method through treatment with calcium chloride, to prepare a DNA library.

With respect to the colonies of this DNA library, colony hybridization is performed in a conventional manner using the aforesaid probe. Thus, a clone bearing the desired DNA fragment can be obtained. Analysis of the nucleotide sequence of the cloned DNA fragment by the method of Messing et al. (Nucleic Acids Res., 9, 309 (1981)) or by the method of Maxam et al. (Methods Enzymol., 65, 499 (1980)), allows for the determination of the entire nucleotide sequence of *Mycobacterium kansasii*-derived α antigen gene. This α antigen can be utilized as a marker gene to check for secretion from mycobacteria since it has been shown that the α antigen has an antigenic determinant specific for *Mycobacterium kansasii*. Then the region containing putative promoter and signal sequence of α antigen may be excised from the cloned fragment using appropriate restriction enzymes.

The heterologous polypeptides which are secreted according to the present invention include β-lactamase derived from *Escherichia coli*, various hormones derived from higher animal, lymphokines represented by human interleukin 2, and antigenic proteins of the AIDS virus. Further, when the a antigen derived from *Mycobacterium kansasii* is secreted by using, e.g., *Mycobacterium bovis* BCG as a host, the produced a antigen derived from *Mycobacterium kansasii* becomes a heterologous polypeptide. That is, even though the host belongs to the same genus as Mycobacterium, the above case falls within the expression and secretion of the heterologous polypeptide according to the present invention so long as a polypeptide from a microorganism of different species is expressed. In addition, for example a fused polypeptide of β-lactamase of *Escherichia coli* and human interleukin 2, also is a heterologous polypeptide of the present invention. Furthermore, a fused polypeptide of *Mycobacterium kansasii*-derived α antigen and B cell epitope of HIV-1 gag antigen is a heterologous polypeptide of the present invention.

To obtain the DNA sequence encoding these heterologous polypeptides, the structural gene may be excised from a plasmid in which the gene for each of these heterologous polypeptides is cloned, using appropriate restriction enzymes. Alternatively, the structural gene may be artificially synthesized.

The replicator region necessary for replication in bacteria is not particularly limited as long as it is derived from a plasmid capable of replicating in mycobacteria. For example, plasmid isolated from mycobacteria may be employed. A shuttle vector of *Escherichia coli*-mycobacteria obtained by fusing vector pIJ666 of *Escherichia coli* with plasmid pAL5000 derived from *Mycobacterium fortuitum* may also be utilized. In addition, a shuttle vector of *Escherichia coli*-mycobacteria obtained by fusing vector pBR322 or pUC18, etc. of *Escherichia coli* with plasmid pAL5000 derived from *Mycobacterium fortuitum* may further be utilized.

These DNA sequences are introduced into the appropriate cloning site, which does not exist in a region of replication origin of plasmid replicable in mycobacteria, in the order: the DNA fragment containing the promoter sequence; the DNA sequence encoding signal peptide and the structural gene of the heterologous polypeptide, from the 5' end, using DNA ligase.

For construction of such a mycobacterial secretory expression vector, there may be used a plasmid isolated from various species of mycobacteria and containing a replicator region capable of replication in mycobacteria. Preferably, the plasmid is fused with a plasmid containing a replicator region capable of replication in *Escherichia coli* (e.g., pBR322, pUC18, etc.) and the fused plasmid is marked with a drug-resistance marker gene capable of expression in both mycobacteria and *Escherichia coli*. An example of such a plasmid with marker is vector pIJ666-pAL5000 bearing genes resistant to kanamycin and chloramphenicol (Snapper et al, Proc. Natl. Acad. Sci. U.S.A., 85, 6987 (1988)). Next the promoter which can function in mycobacteria and the DNA fragment containing a gene encoding signal peptide are introduced into the plasmid described above. Preferably these sequences are derived from proteins (for example, α antigen, MPB64 protein, MPB70 protein, etc.) actually secreted from mycobacteria such as BCG. They are introduced into the plasmid described above at an appropriate cloning site and the DNA fragments encoding various heterologous polypeptides are introduced downstream of the signal sequence, using a synthetic adaptor if necessary, whereby a vector for secreting the heterologous polypeptides is constructed.

By introducing the polypeptide-secretory expression vector of the present invention into mycobacteria, the secretory ability of this polypeptide is imparted to BCG. The expression vector is introduced into mycobacteria by electroporation at an electric field intensity of 6.25 KV/cm or more, in a manner similar to the method of Snapper et al. (Proc. Natl.

Acad. Sci., U.S.A., 85, 6987 (1988)), whereby the transformant is obtained.

Examples of the mycobacteria used as hosts are the rapid growing mycobacteria such as *Mycobacterium smegmatis*. In addition, slow growing mycobacteria such as BCG, *Mycobacterium tuberculosis*, and atypical acid-fast bacteria, may be used. However, it is desired to use mutants with restriction minus by a treatment with a variation agent such as nitrosoguanidine or the like or by UV irradiation.

Next, the resulting transformant is cultured in an aerobic medium, whereby the heterologous polypeptide can be secreted in the culture supernatant. Culture can be carried out by known methods for culturing mycobacteria used as a host. After culture, the produced polypeptide may be isolated and purified in a conventional manner, if necessary.

The transformant can be used as a vaccine. In this case, the transformant is used after its activity has been reduced by heating, treatment with formalin, etc., if necessary. As a medium in which the transformant is suspended, physiological saline, phosphate buffer, etc., may be used and its concentration is approximately 0.01 to 0.8 mol/liter.

In the secretory expression vector obtained according to the present invention, the promoter sequence is mandatory since messenger RNA corresponding to the fused polypeptide composed of signal peptide and heterologous polypeptide is synthesized by RNA polymerase of mycobacteria. Furthermore, the sequence coding for the signal peptide is indispensable for passing the heterologous polypeptide through the cytoplasmic membrane of mycobacteria to be extracellularly secreted. In this way the structural gene of the heterologous polypeptide is extracellularly secreted from mycobacteria. Furthermore, DNA in the replicator region is required so that the vector is replicated and succeeded by daughter cells at the time when mycobacteria divide and proliferate, and the heterologous polypeptide is expressed and secreted also in the daughter cells.

Other features of the invention will become apparent in the course of the following descriptions of exemplary embodiments which are given for illustration of the invention and are not intended to be limiting thereof.

EXAMPLES

In the present text, the following abbreviations are used:

A: adenine; C: cytosine; G: guanine; T: thymine; DNA: deoxyribonucleic acid; dCTP: deoxycytidine triphosphate; EDTA: ethylenediaminetetraacetic acid; kb: killo base; SDS: sodium dodecyl sulfate; SSC: 0.15 M sodium chloride and 0.015 M sodium citrate (pH 7.0); TE: buffer containing 10 mM Tris-hydrochloride and 1 mM EDTA (pH 8.0); IPTG: isopropyl-β-D-thiogalactoside; X-gal: 5-bromo-4-chloro-3-indolyl-β-D-galactopyranoside.

Example 1
Preparation of Secretory Expression Vector (1) Preparation of DNA Fragment Containing DNA Encoding α Antigen Gene Derived from *Mycobacterium kansasii*

*Mycobacterium kansasii* ATCC 12478 strain was cultured in 1 liter of Sauton medium (composition: 0.4% of asparagine, 0.2% of citric acid, 0.28% of sodium citrate, 0.05% of potassium phosphate, 0.05% of magnesium sulfate, 0.005% of ammonium ferrous citrate, 6% of glycerine) at 37° C. The cells in the exponential growth phase were collected by centrifugation. The cells obtained were suspended in 5 ml of TE and 5 mg of lysozyme was added to the suspension followed by incubation at 37° C. for 15 minutes. Then, after 0.5 ml of 10% SDS aqueous solution was added thereto, the mixture was extracted 3 times with 6 ml of a mixture of phenol:chloroform:isoamyl alcohol= 25:24:1. The resulting aqueous phase was mixed with 10 ml of ethanol and the precipitated DNA was wound up around a glass rod. The DNA was dissolved in 6.6 ml of TE, and 7 g of cesium chloride and 0.7 ml of an aqueous solution of ethydium bromide (5 mg/ml) were added to the solution to dissolve. The solution was placed in a centrifuge tube (manufactured by Beckmann Company in U.S.A., Quick Seal Tube) and centrifuged at 60,000 rpm for 6 hours. A band of chromosomal DNA was collected from the upper part of the centrifuging tube. The DNA solution was dialyzed in TE and desalted to give pure chromosomal DNA of *Mycobacterium kansasii*.

Next, 20 μg of plasmid pP-1 (J. Bacteriol., 170, 3847 (1988)) into which the 0.8 kb Pst I fragment corresponding to $Leu^{11}$-$Gln^{279}$ of α antigen gene of BCG was subcloned, was fully digested with restriction enzymes Pst I and Xho I followed by fractionation by 1% agarose gel electrophoresis. The fraction was applied to DE-81 paper method (J. Bacteriol., 170, 3847 (1988)) to recover the Pst I-Xho I fragments of 490 bp and 310 bp. After extraction was performed twice, each with phenol and chloroform, a 2.5-fold volume of ethanol was added to cause precipitation. After drying under reduced pressure, the precipitates were dissolved in 20 μl each of TE. To 12 μl of the solutions were added 4 μl of buffer having 10-fold concentration in the nick translation kit (manufactured by Takara Shuzo Co., Ltd.), 1 μl of enzyme solution, 10 μl of [α-$^{32}$P] dCTP (manufactured by Amersham Co., 3,000 Ci/mmol) and 13 μl of distilled water. The mixture was reacted at 15° C. for 2 hours. The reaction mixture was extracted once with phenol. Then, the aqueous phase was collected and 30 μl of calf thymus-derived DNA solution (1 mg/ml) and 10 μl of 3 M sodium acetate were added and ethanol was further added to the aqueous phase. The precipitates were collected and dissolved in 100 μl of TE to prepare $^{32}$P-labeled probe solutions (Probe A: 490 bp fragment, Probe B: 310 bp fragment).

Three μg of the aforesaid chromosomal DNA was fully digested with restriction enzyme Kpn I followed by fractionation by 0.8% agarose gel electrophoresis. Thereafter, the fraction was fixed onto a nylon membrane filter (manufactured by NEN Company, Gene Screen Plus) in a conventional manner by Southern transfer (J. Mol. Biol., 98 503 (1975)) to prepare a DNA-bound filter. The filter was immersed in a hybridization solution (Denhardt solution of 5-fold concentration (0.1% of Ficoll 400, 0.1% of polyvinylpyrrolidone, 0.1% of bovine serum albumin) SSC in 5-fold concentration, 0.1% of SDS solution and 10 μg/ml of calf thymus-derived DNA) and 20 μl of the $^{32}$P-labeled probe described above was added thereto followed by incubating at 58° C. for 16 hours. After shake-washing in 2-fold concentration SSC-0.1% SDS solution at room temperature for 10 minutes, washing in 0.1 fold concentration SSC-0.1% SDS solution at 60° C. for 20 minutes was repeated four times. After washing, the filter was dried at room temperature and autoradiographed to detect the Kpn I fragment of 5.5 kb.

To clone this fragment, 20 μg of the chromosomal DNA of *Mycobacterium kansasii* was fully digested with Kpn I followed by fractionation through 0.8% agarose gel electrophoresis. Then, the fragment in the range of 5.0 to 6.3 kb was recovered by the DE-81 paper method. After treatment with phenol and chloroform and then precipitation with ethanol, the precipitates were dissolved in 20 μl of TE. A mixture of 4 μl of the solution, 0.2 μg (2 μl) of the pUC18/Kpn I cleavage product, 38 μl of Solution A and 6 μl of Solution B of a DNA Ligation Kit (manufactured by Takara Shuzo Co., Ltd.) was reacted at 16° C. for 30 minutes. After 20 μl of the reaction solution was added to 100 μl of *E. coli* JM109 competent cells (manufactured by Takara Shuzo Co., Ltd.), the mixture was incubated at 0° C. for 40 minutes, then at 42° C. for 90 seconds and then at 0° C. for 5 minutes. Thereafter, 500 μl of L-broth medium (composition: 1% of bacto-trypton, 0.5% of yeast extract, 0.5% sodium chloride and 0.1% of glucose) was added, followed by incubating at 37° C. for an hour. A portion of the culture medium was taken and applied to L-agar plate (L-broth+1.5% agar) containing 50 μg/ml of ampicillin, 0.1 mM IPTG and 0.004% of X-gal. Incubation at 37° C. for 16 hours gave 200 white colonies which were resistant to ampicillin and did not retain β-galactosidase activity. The colonies were subjected to colony hybridization using Probe A and Probe B in a conventional manner (Methods Enzymol., 68, 379 (1979)) to give one positive clone. From this clone, plasmid was extracted and named pKA52.

After digesting pKA52 with various restriction enzymes, the fragments were analyzed by the Southern hybridization. From the analysis, it was expected that the α antigen gene derived from *Mycobacterium kansasii* would be located on the 2.0 kb Hinc II fragment. Thus, the fragment was isolated, purified and then subcloned to Hinc II site of pUC18 (plasmid pKAH20). Its nucleotide sequence was determined using the dideoxy method (Proc. Natl. Acad. Sci., U.S.A., 74 5463 (1977)), whereby the presence of the nucleotide sequence corresponding to the N-terminal amino acid sequence of the α antigen purified from the culture medium of *Mycobacterium kansasii* was confirmed. The entire nucleotide sequence and the deduced amino acid sequence are shown in FIG. 1, in which the expected promoter sequence is designated −35, −10.

(2) Preparation of DNA Fragment Containing *E. coli* β-Lactamase Gene

As shown in FIG. 3, the ApaL I fragment of 1.2 kb generated by digesting plasmid pUC18 (10 μg) with ApaL I was isolated and purified by the DE-81 paper method, treatment with phenol and chloroform, and precipitation with ethanol described above. The purified ApaL I fragment was dissolved in 20 μl of TE. On the other hand, two oligonucleotides:

5'AACGCTGGTGAAAGTAAAAGATGCTGAA-
GATCAGTTGGG3'

5'TGCACCCAACTGATCTTCAGCATCTTT-
TACTTTCACCAGCGTT3' corresponding to $Thr^4$-$Ala^{17}$ of β-lactamase and constructing an adaptor for connecting the ApaL I site and the Hinc II site were synthesized using an automated DNA synthesizer (Applied Biosystems Inc., U.S.A., Model 380A). After all the protective groups except a dimethoxytrityl group were removed, purification was performed by reverse phase medium pressure column chromatography (conditions: C-18 silica gel column was used and as the moving phase, a density gradient solution composed of acetonitrile was used in 100 mM triethylamine acetate buffer (pH 7.0)). Then, after the dimethoxytrityl group was removed by 80% acetic acid, purification was performed by reverse phase HPLC (conditions: YMC PACK AM-314 ODS column was used and as the moving phase, a density gradient solution composed of acetonitrile was used in 100 mM triethylamine acetate buffer (pH 7.0) followed by freeze drying). The two oligonucleotides thus obtained were taken by 250 pmols each and reacted at 37° C. for an hour with 15 units of polynucleotide kinase in kinase reaction buffer (50 mM Tris-hydrochloride buffer (pH 7.5), 10 mM magnesium chloride, 10 mM dithiothreitol, 1 mM ATP). From the respective reaction mixtures, 50 pmols each was mixed and heated at 70° C. for 5 minutes and then annealed.

Thus, oligonucleotide adapters having nucleotide sequences:

5'-AACGCTGGTGAAAGTAAAAGATGCTGAA-
GATCAGTTGGG-3'

3'-TTGCGACCACTTTCATTTTCTACGACT-
TCTAGTCAACCCACGT-5' were obtained. About 40 pmols of this annealing mixture was ligated with 2 μl (0.5 μg) of the aforesaid 1.2 kb Apal I fragment solution and about 0.1 μg of the Hinc II digested pUC18 by the DNA ligation kit in the same manner as described in (1) to give plasmid pUCLAC-1. After 10 μg of this plasmid was cleaved with Hinc II, the resulting Hinc II fragment of 1.3 kb was likewise isolated and purified. After treatment with phenol and chloroform and precipitation with ethanol, the precipitates were dissolved in 20 μl of TE to give β-lactamase gene fragment containing the structural gene downstream from $Thr^4$.

(3) Construction of *Mycobacterium Kansasii*-Derived α Antigen-Secretory Expression Vector

*Escherichia coli*-mycobacteria shuttle vector pIJ666-pAL5000 (5 μg) was digested with Kpn I. After heat treatment at 65° C. for 5 minutes to inactivate the enzyme, ethanol precipitation was performed. After drying, the precipitates were dissolved in 192 μl of 50 mM Tris-hydrochloride buffer (pH 8.5) and 4 μl (2 U) of alkali phosphatase (*E. coli* C-75) was added to the solution. The mixture was incubated at 65° C. for an hour. Further, 4 μl of alkali phosphatase was added to the mixture. After incubating for an hour, the mixture was treated with phenol and with chloroform and precipitated with ethanol. The precipitates were dissolved in 20 μl of TE to prepare a vector solution. On the other hand, a Kpn I linker (manufactured by Takara Shuzo Co., Ltd.) was ligated at both ends of the 2.0 kb Hinc II fragment derived from plasmid pKAH20 prepared in (1). The ligation product was cleaved with Kpn I to give the Kpn I fragment of 2.0 kb. Using DNA ligation kit, 0.2 μg of the Knp I fragment was ligated with 1 μl (0.1 μg) of the aforesaid vector solution to give *Mycobacterium Kansasii*-derived α antigen-secretory expression vector pIJK-1. Construction of this vector is shown in FIG. 2.

(4) Construction of *Escherichia coli*-Derived β-Lactamase-Secretory Expression Vector The already cloned 3.6 kb Sal I fragment containing a gene of secretory antigen MPB70 of BCG (FEMS Microbiol. Lett., 273–276 (1989)) was cleaved with Sma I. Since promoter and the region encoding signal peptide were contained in the resulting 0.8 kb Sma I fragment, the fragment was purified by the DE-81 paper method described above. Using DNA ligation kit, 0.3 μg of the purified fragment was ligated with 0.1 μg of the SmaI-digested pUC18.

The resulting product was transformed into *E. coli* JM 109 competent cells. By preparing recombinant plasmid from the transformant, a plasmid to which the 0.8 kb Sma I fragment was subcloned was obtained and named pSma800 (cf. FIG. 3). This plasmid, 5 μg, was digested with restriction enzymes Not I and Hinc II. The resulting Not I-Hinc II fragment of 3.4 kb was purified by the DE-81 paper method. The fragment contained the promoter and the region encoding 29 amino acids out of 30 amino acids of the signal peptide of MPB70 and lacked the sequence for the remaining one amino acid residue of signal peptide (FIG. 3).

Next, in order to introduce the 1.3 kb Hinc II fragment containing the sequence for downstream of Thr$^4$ of β-lactamase prepared in (2) into the downstream of the signal sequence of MPB70, an adaptor compensating for the sequence corresponding to the C-terminal Ala of signal peptide and His$^1$-Glu$^3$ of β-lactamase and capable of ligating the Not I site with the Hinc II site was prepared. That is, two oligonucleotides:

5'-GGCCGCACACCCAGA-3' and 5'-TCTGGGTGTGC-3' were synthesized, purified, subjected to kinase reaction and annealed in the same manner as in (2) to give an adaptor having the following nucleotide sequence:

5'-GGCCGCACACCCAGA-3'

3'-CGTGTGGGTCT-5'

Figure 1A:
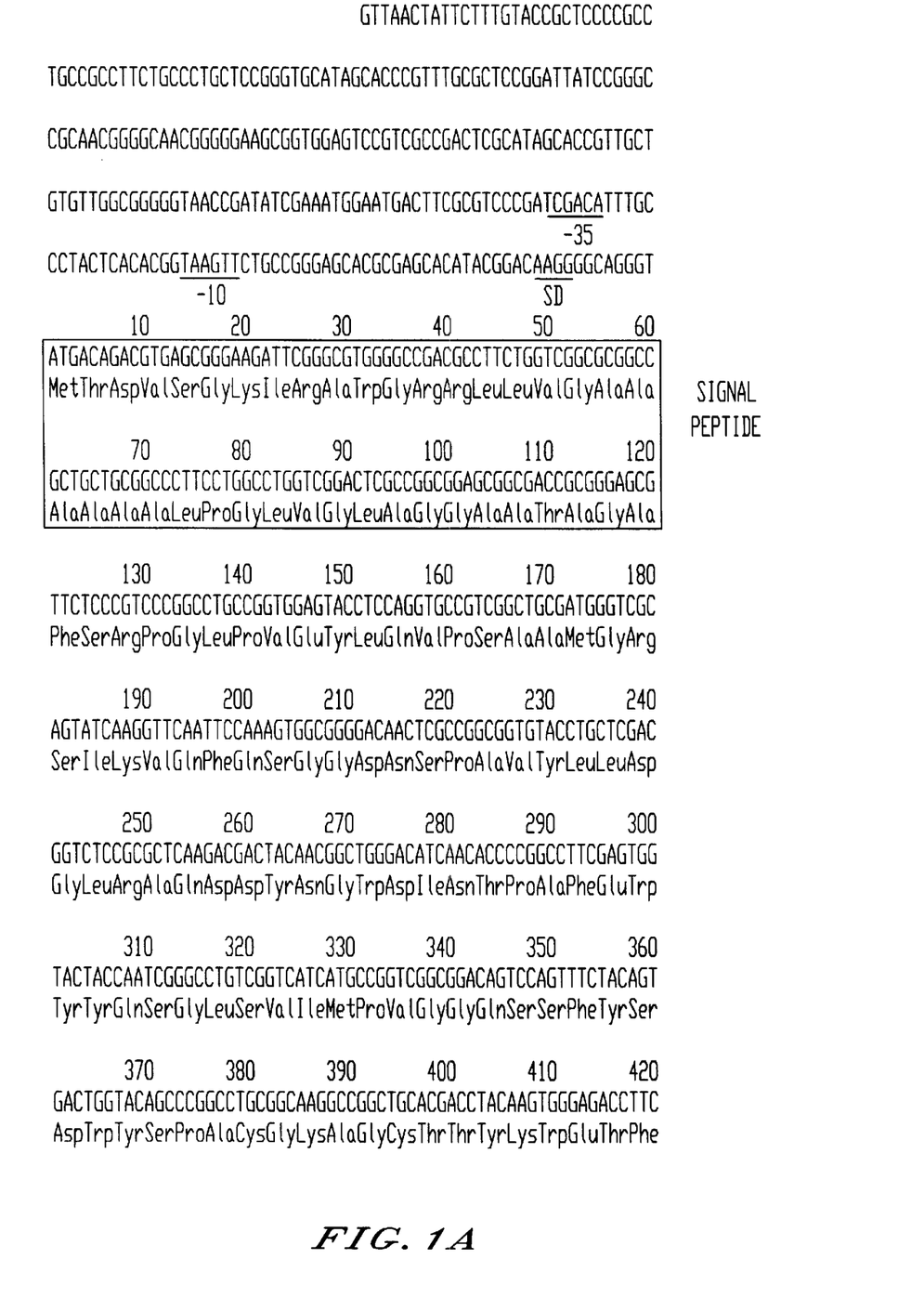
FIG. 1 shows a nucleotide sequence of *Mycobacterium kansasii*-derived α antigen gene and a deduced amino acid sequence, wherein the portion surrounded by line indicates a region of signal peptide.
Figure 1B:
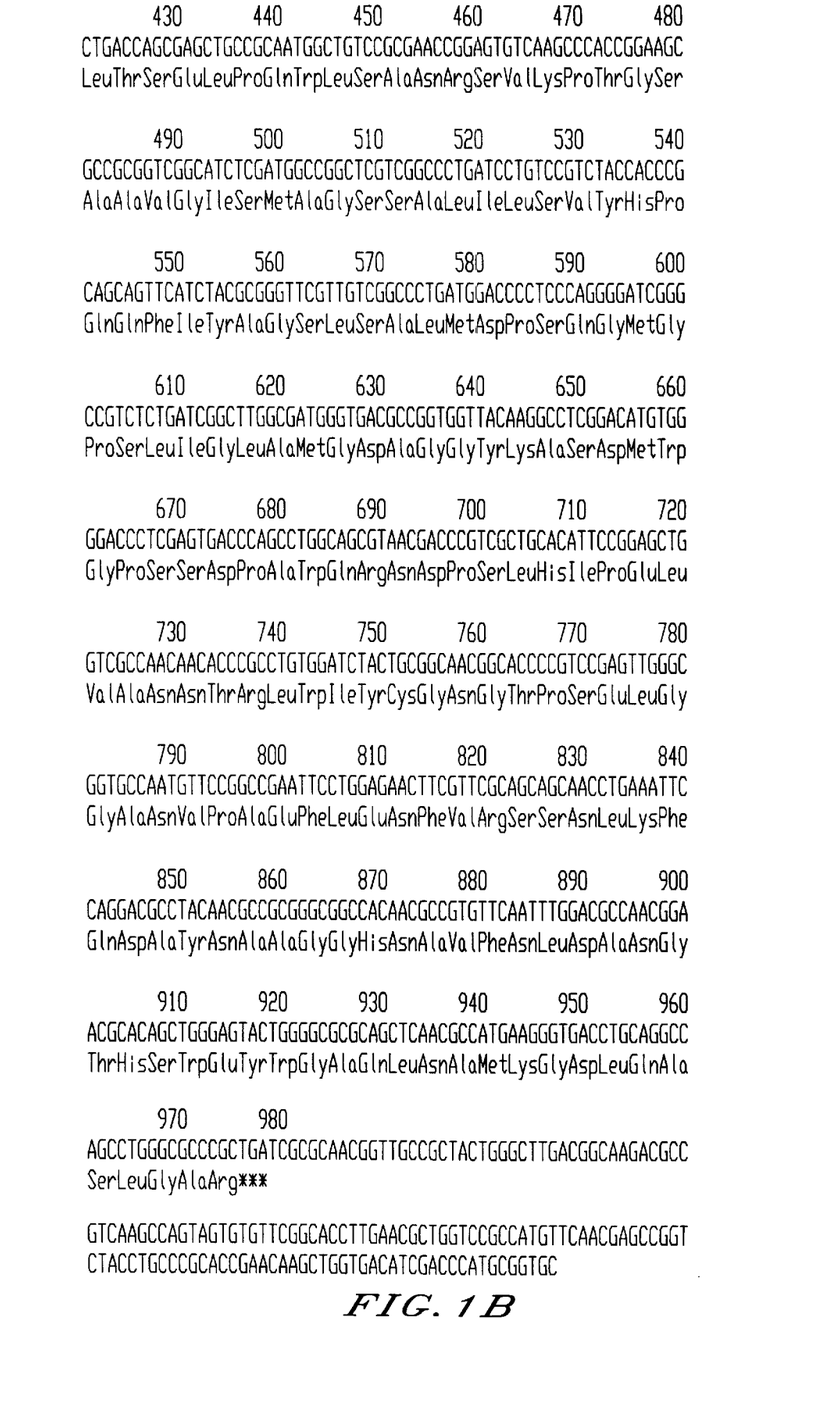
Figure 2:
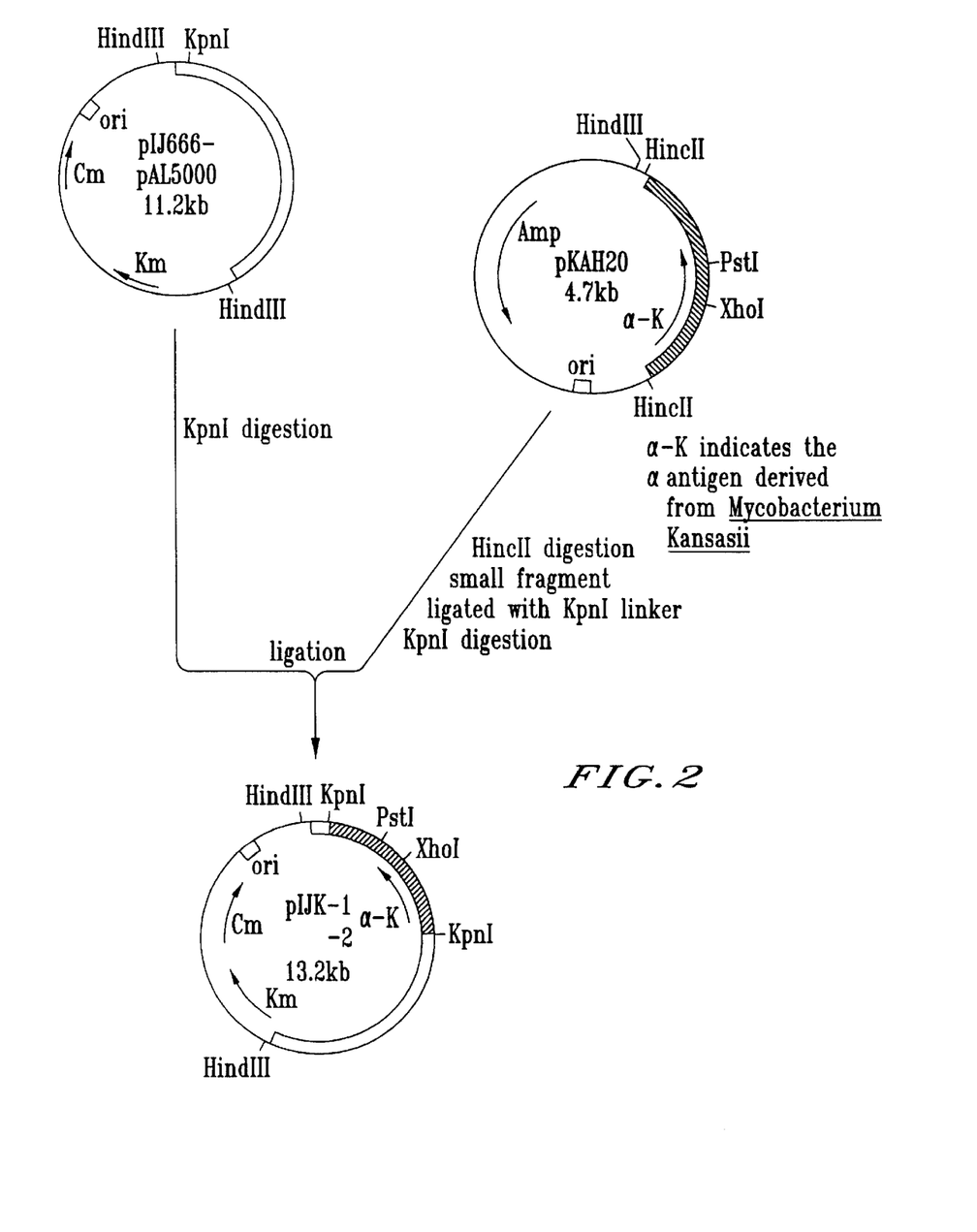
FIG. 2 shows construction of secretory expression vector pIJK-1 for the *Mycobacterium kansasii*-derived α antigen.
Figure 3:
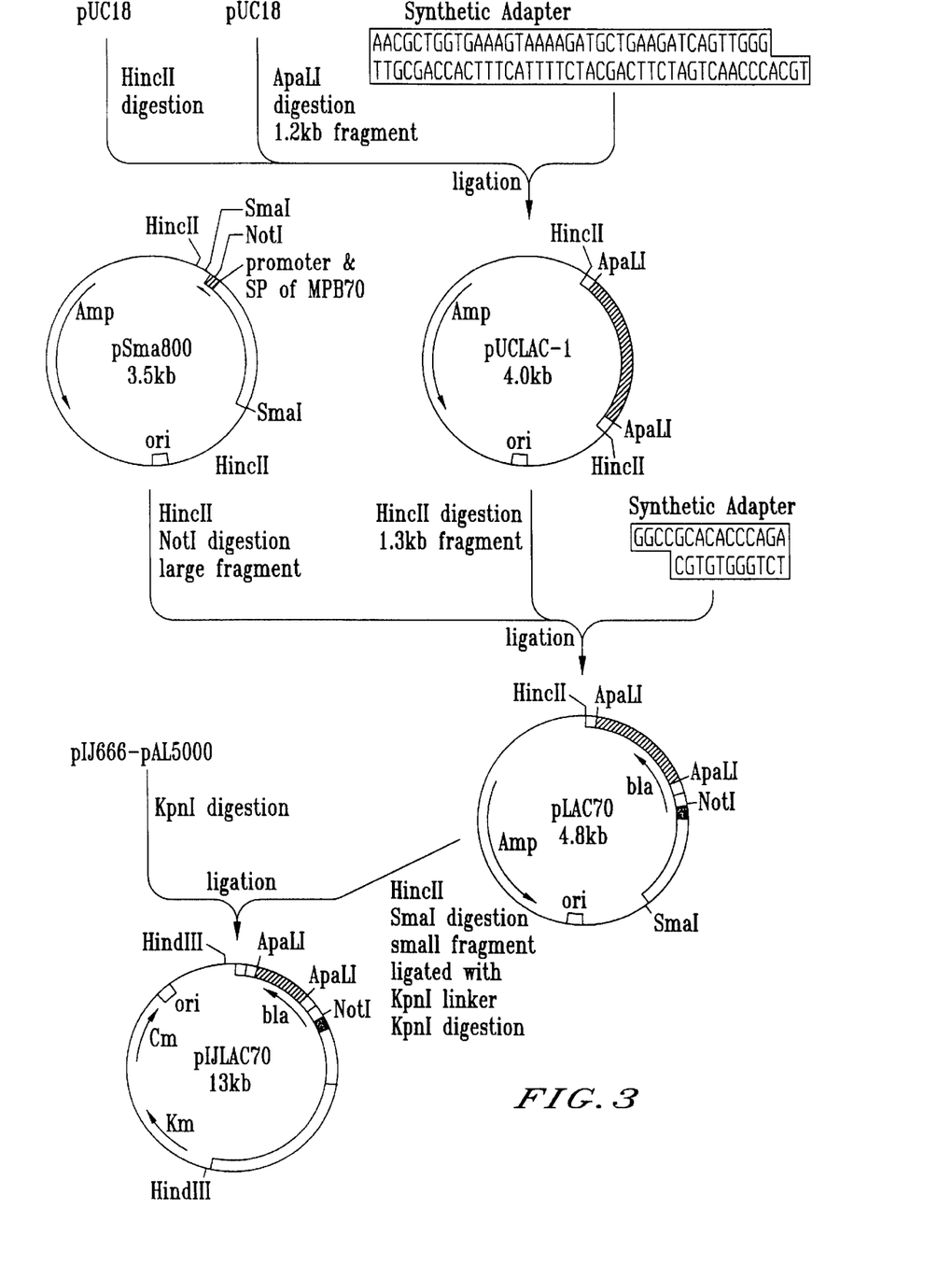
FIG. 3 shows construction of secretory expression vector pIJLAC70 for the *Escherichia coli* β-lactamase.

About 40 pmols of this adaptor was ligated with 0.1 μg of the 3.4 kb Not I-Hinc II fragment and 0.3 μg of the 1.3 kb Hinc II fragment using DNA ligation kit to give plasmid pLAC70 having the complete structural gene of β-lactamase immediately downstream of the signal peptide region of MPB70 (FIG. 3).

pLAC 70 (20 μg) was fully digested with Sma I and Hinc II. The resulting 2.1 kb Sma I-Hinc II fragment was isolated and purified by the DE-81 paper method. In a manner similar to (3), 0.3 μg of the purified fragment was ligated with Kpn I linkers. Then, the ligation product was cleaved with Kpn I to give the 2.1 kb kpn I fragment.

The 2.1 kb fragment was then ligated with 0.1 μg of dephosphorylated KpnI-digested shuttle vector prepared in (3) using DNA ligation kit to give *Escherichia coli*-derived β-lactamase-secretory expression vector pIJLAC70 (FIG. 3).

Example 2
Heterogeneous Polypeptide Secreted from BCG (1) Secretion of *Mycobacterium kansasii*-Derived α Antigen from BCG.

*Mycobacterium bovis* BCG Tokyo strain was cultured at 37° C. in 8 ml of Middlebrook 7H9 medium containing albumin-dextrose complex and 0.05% Tween 80 (hereafter simply referred to as 7H9 medium) (manufactured by Difco Company). At the time when OD$_{590}$ reached 0.1, the cells were collected by centrifugation and suspended in 0.8 ml of electroporation buffer (7 mM sodium phosphate/272 mM mannitol, pH 7.2, 0.5% Tween 80). To the BCG suspension was added α antigen-secretory expression vector pIJK-1 (1 μg) prepared in Example 1 (3). The mixture was charged in an electroporation cuvette. After incubating at 0° C. for 10 minutes, electroporation was performed for 500μ seconds with a square wave having an electric field intensity of 7,000 V/cm (electric cell fusion apparatus Model SSH-1 manufactured by Shimadzu Seisakusho Ltd.). After the electroporation, the cells were incubated at 0° C. for 10 minutes and 0.8 ml of 7H9 medium was added to the cells. The mixture was incubated at 37° C. for a further 2 hours and then applied onto 7H10 agar (manufactured by Difco Company) plate containing 10 μg/ml of kanamycin. Incubation at 37° C. for 30 days gave transformant in 100 colonies/μg DNA.

After the transformant was stationary cultured at 37° C. for 21 days in 50 ml of Sauton medium (containing 10 μg/ml of kanamycin), the cells were removed through a millipore filter (0.45 μm). One milliliter of 10% trichloroacetic acid aqueous solution was added to 1 ml of the culture supernatant and the mixture was incubated at 0° C. for 20 minutes. Centrifugation was carried out at 12,000 rpm for 10 minutes. After the precipitated protein was washed with chilled acetone, the protein was dried in vacuo.

Figure 4:
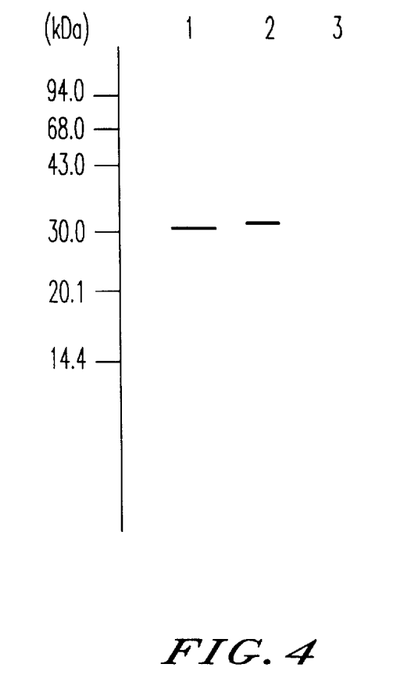
FIG. 4 indicates analysis data by the Western blot technique for confirming the secretion of *Mycobacterium kansasii*-derived α antigen.

The precipitates were dissolved in 20 μl of sample buffer for SDS-polyacrylamide gel electrophoresis (60 mM Tris, 2% of SDS, 5% of 2-mercaptoethanol, 10% of glycerol, 0.1% of bromophenol blue) by heating at 95° C. for 5 minutes. The solution was analyzed by SDS-polyacrylamide gel electrophoresis and the Western blot technique. The results are shown in FIG. 4. In the figure, lane 1 presents α antigen derived from *Mycobacterium kansasii* and lanes 2 and lane 3 were obtained with the respective culture supernatants of pIJK-1/BCG and pIJ666-pAL5000/BCG. Further, a band around 30 kDa in the figure is *Mycobacterium kansasii*-derived α antigen. In the Western blot analysis using anti-α-K (purified α antigen derived from *M. kansasii*) absorbed by α-T (purified α antigen derived from *M. tuberculosis*), no positive band was observed in BCG harboring pIJ666-pAL5000 (FIG. 4, lane 3), whereas in BCG harboring pIJK-1 (*Mycobacterium bovis* BCG Tokyo (pIJK-1)), a positive band was observed at the position of similar molecular weight to that of the purified α-K antigen (FIG. 4, lane 2), indicating that α antigen derived from *Mycobacterium kansasii* is secreted from BCG.

(2) Secretion of *Escherichia coli*-Derived β-Lactamase from BCG

Using 1 μg of β-lactamase-secretory vector pIJLAC70 constructed in Example 1 (4), the vector was transformed into BCG by electroporation in a manner similar to (1). After the resulting kanamycin-resistant transformant was cultured in 50 ml of Sauton medium at 37° C. for 21 days, the cells were removed through a millipore filter (0.45 μm). To the culture supernatant was slowly added 28.05 g of ammonium sulfate with gentle stirring to dissolve. The solution was incubated at 4° C. overnight. Then, the precipitated protein was centrifuged and dissolved in 5 ml of 100 mM potassium phosphate buffer (pH 7.0). The solution was then dialyzed in the same buffer for desalting, to prepare a crude enzyme solution.

Using a portion of the crude enzyme solution, decomposition of benzylpenicillin was carried out to estimate the β-lactamase activity by observing the reduction in absorbance at 240 nm. The activity was very low in the crude enzyme solution prepared from the culture medium of BCG harboring pIJ666-pAL5000. Whereas in the culture of BCG harboring pIJLAC70, high β-lactamase activity was observed. Thus, 1 ml of the crude enzyme solution was precipitated with trichloroacetic acid as in (1) and the protein was recovered. In SDS-polyacrylamide gel electrophoresis of the protein, a marked band was observed at the position showing a theoretical molecular weight of 29,000 for β-lactamase, indicating that *Escherichia coli*-derived β-lactamase was secreted from BCG.

Example 3
Secretion of Fused Protein from BCG (1) Construction of a Vector to Secrete Fused Protein Composed of *Mycobacterium kansasii*-Derived α Antigen HIV-1 gag Antigen Firstly, among B cell epitopes of p17 protein of HIV (causative virus of AIDS) gag antigen, DNA fragments containing the sequence encoding one epitope of 8 amino acids: Glu$^{12}$-Leu-Asp-Arg-Trp-Glu-Lys-Ile$^{19}$ recognized by an anti-HIV-1 p17 monoclonal antibody (manufactured by Chemicon International Company) and also encoding the portion: Ala$^{280}$-Arg$^{285}$ of *Mycobacterium kansasii*-derived α antigen were synthesized. That is, two oligonucleotides:

5'-GGGCGAGCTGGACCGGTGGTGGGAGAA-
GATCGCCAGCCTGGGCGCCCGCTGA-3' (49-mer)

and

Figure 5:
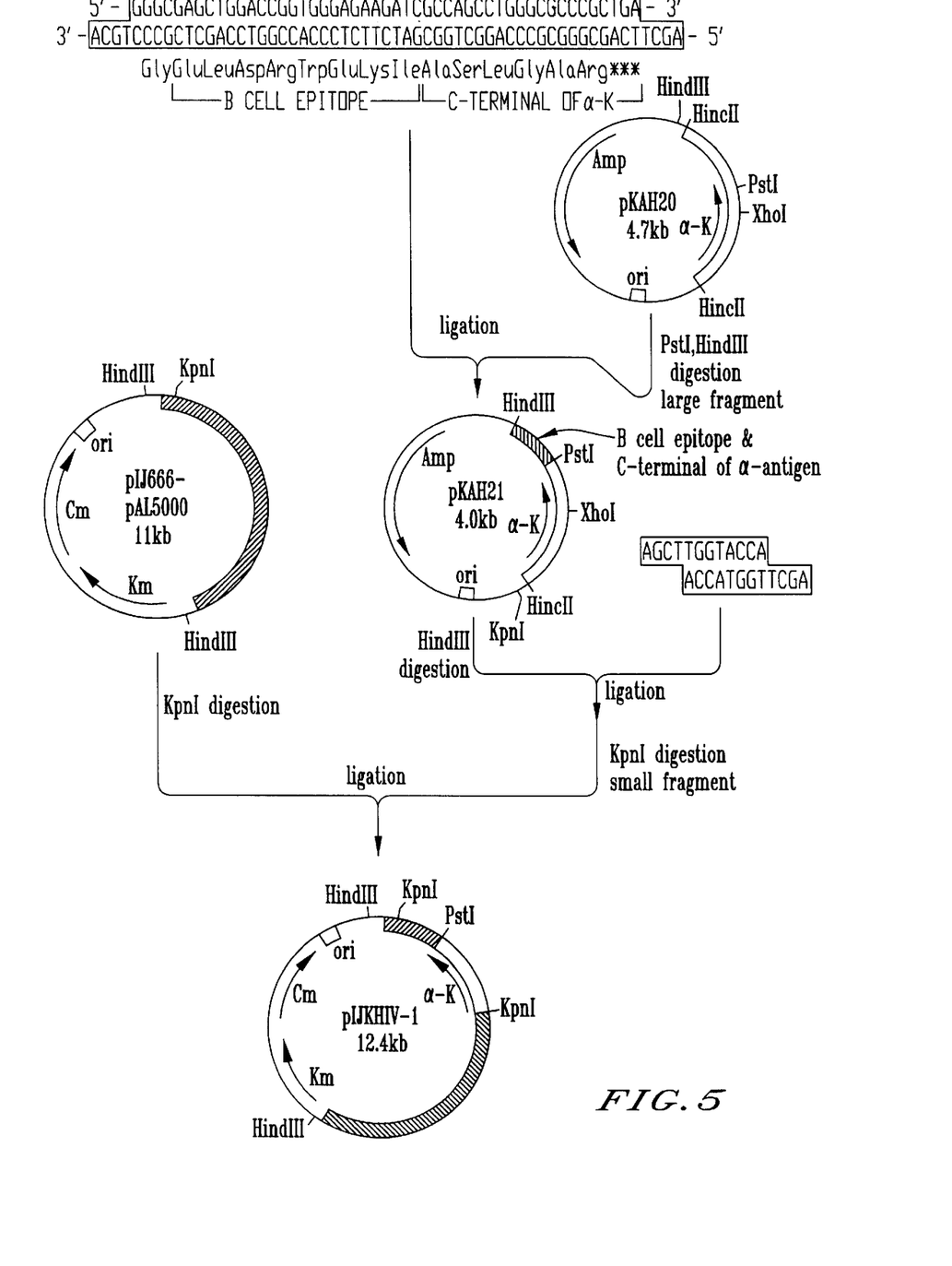
FIG. 5 shows construction of secretory expression vector of *Mycobacterium kansasii*-derived α antigen-HIV 1 gag antigen p17 B cell epitope fused protein.

5'-AGCTTCAGCGGGCGCCCAGGCTGGC-
GATCTTCTCCCACCGGTCCAGCTCGCCCTGCA-3' (57-mer)

were synthesized, purified, subjected to kinase reaction and annealing in a manner similar to Example 1 (2) to give the desired Pst I-Hind III DNA fragments (cf. FIG. 5).

The aforesaid pKAH20 (5 μg) containing *Mycobacterium kansasii*-derived α antigen gene was fully digested with Pst I and Hind III. The resulting Pst I-Hind III fragment of 4.0 kb was purified by the DE-81 paper method. Using the DNA ligation kit, 0.1 μg of the purified fragment was ligated with 0.1 pmol of the DNA fragment corresponding to the HIV-1 epitope. The ligation product was transformed to *E. coli* MJ109 competent cells. By preparing recombinant plasmid from the transformant, there was obtained plasmid pKAH21 having a gene of the fused protein in which 8 amino acids of the B cell epitope of HIV-1 gap antigen p17 protein, namely:

Glu-Leu-Asp-Arg-Trp-Glu-Lys-Ile was inserted between $Gln^{279}$ and $Ala^{280}$ of *Mycobacterium kansasii*-derived α antigen (FIG. 5). Using the DNA ligation kit, 0.1 μg of the fully digested product of this plasmid with Hind III was ligated with 0.1 pmol of chemically synthesized Kpn I linker having the following nucleotide sequence:

5'-AGCTTGGTACCA-3'

3'-ACCATGGTTCGA-5' prepared by synthesizing, purifying, subjecting to kinase reaction and annealing in a manner similar to Example 1 (2). The ligation product was transformed to *E. coli* JM109 competent cells. The recombinant plasmid, 10 μg, prepared from the resulting transformant was fully digested with Kpn I. The resulting Kpn I fragment of 1.4 kb was purified by the DE-81 paper method and dissolved in 20 μl of TE to prepare a solution of the fused protein gene fragment.

The aforesaid Kpn I-digested vector pIJ666-pAL5000 (1.0 μg) was reacted with 1 μl of the solution of fused protein gene fragment to give secretory vector pIJKHIV-1, which is capable of causing the secretion of *Mycobacterium kansasii*-derived α antigen-HIV-1 gag antigen p17 B cell epitope fused protein (cf. FIG. 5).

(2) Secretion of *Mycobacterium kansasii*-Derived α Antigen-HIV-1 Gag Antigen p17 B Cell Epitope Fused Protein BCG Tokyo strain was transformed with PIJK HIV-1 as described in Example 2 (1) to give a transformant BCG18HIV, (*Mycobacterium bovis* BCG Tokyo (pIJKHIV-1)).

After the transformant was stationary cultured at 37° C. for 28 days in 100 ml of Sauton medium (containing 10 μg/ml of kanamycin), the cells were removed by centrifugation. While stirring, 56.1 g of ammonium sulfate was slowly added to the culture supernatant to dissolve. The solution was incubated at 4° C. overnight. Then, the precipitated protein was centrifuged and dissolved in 5 ml of 100 mM potassium phosphate buffer (pH 7.0). One milliliter of the solution was taken and 1 ml of 10% trichloroacetic acid aqueous solution was added. After incubating at 0° C. for 20 minutes, centrifugation was carried out at 12,000 rpm for 10 minutes. The precipitated protein was washed with cold acetone and then dried in vacuo.

Figure 6:
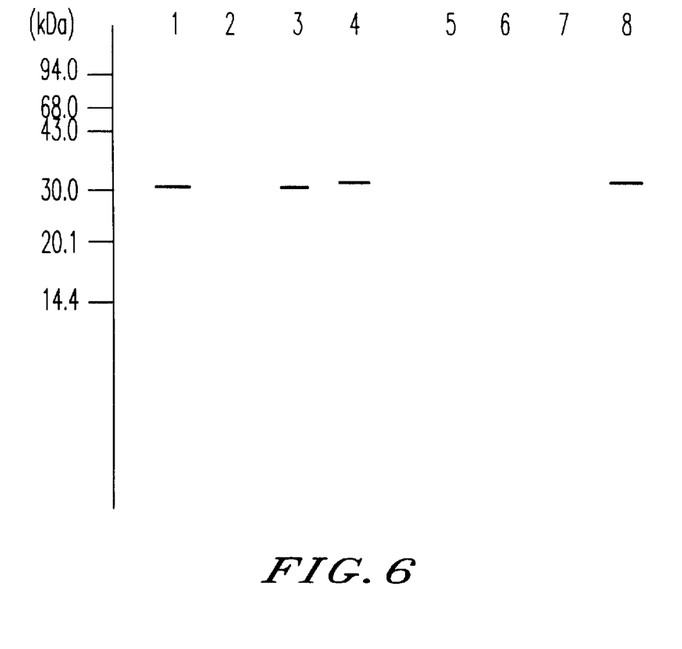
FIG. 6 shows the results of Western blot analysis for confirming that the *Mycobacterium kansasii*-derived α antigen-HIV 1 gag antigen p17 B cell epitope fused protein is secreted.

The precipitates were analyzed by SDS-polyacrylamide gel electrophoresis and Western blotting in a manner similar to Example 2 (1). The results are shown in FIG. 6. In the figure, lanes 1 and 5 present *Mycobacterium kansasii*-derived a antigen. Lanes 2 and 6, lanes 3 and 7, and lanes 4 and 8 were obtained with the respective culture supernatants of BCG bearing pIJ666-pAL5000, pIJK-1 and pIJKHIV-1-containing BCG (BCG18HIV). Lanes 1 through 4 and lanes 5 through 8 indicate Western blotting patterns using the absorbed anti-α-K (abbreviation for anti-*Mycobacterium kansasii*-derived α antigen) antibodies and anti-HIV-1 p17 monoclonal antibody (manufactured by Chemicon International Company), respectively, as primary antibody. When the absorbed anti-α-K antibodies were used, no positive band was observed in pIJ666-pAL5000/BCG as a negative control (lane 2); whereas in pIJK-1/BCG or pIJKHIV-1/BCG, a positive band was observed (lanes 3 and 4).

On the other hand, when the anti-HIV-1 p17 monoclonal antibody was used, a positive band was observed only in pIJK HIV-1/BCG at the position of slightly larger molecular weight than that of α-K, indicating that the fused protein of *Mycobacterium kansasii*-derived α antigen with the B cell epitope of HIV-1 gag antigen p17 protein was secreted from BCG. This BCG transformant might be used as an AIDS vaccine.

The mycobacterial secretory expression vector provided by the present invention is suitable for the development of a recombinant BCG live vaccine by secreting antigenic polypeptides of various infectious microorganisms which cause incurable diseases such as AIDS, malaria, leprosy, etc., in a mature form or as a fused protein. Furthermore, if a protein acting as a major protective antigen to infections with tubercle bacillus were found from the BCG derived antigens in the future, it would be possible to develop BCG vaccine having an improved vaccine effect by incorporating this protein gene into the secretory vector and introducing the vector into BCG.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. A transformant of *Mycobacterium bovis* BCG that secretes a heterologous polypeptide which has been transformed with a vector, said vector comprising:

a promoter, a signal sequence of *Mycobacterium kansasii*-derived α antigen, a DNA nucleotide sequence encoding a heterologous polypeptide, and a replicator region for replication in mycobacteria.

2. A transformant of claim 1, wherein said promoter is of *M. kansasii*-derived α antigen.

3. The transformant of claim 1, wherein said heterologous polypeptide is a B cell epitope of human immunodeficiency virus type 1 gag antigen p17 protein.

4. The transformant of claim 3, wherein said B cell epitope comprises the following amino acid sequence:

Glu-Leu-Asp-Arg-Trp-Glu-Lys-Ile.

5. A method for producing a secreted heterologous polypeptide in *Mycobacterium bovis* BCG, comprising:
(A) culturing in a culture medium host *M. bovis* BCG cells of claim 1;
(B) collecting said cells and culture medium containing the secreted heterologous polypeptide from the culture.

6. The method of claim 5, further comprising isolating the secreted heterologous polypeptide from the cells and culture medium.

7. The method of claim 5, wherein said promoter is from *M. kansasii*-derived α antigen.

8. The method of claim 7, wherein said heterologous protein comprises a B cell epitope of the human immunodeficiency virus type 1 gag antigen p17 protein.

9. The method of claim 8, wherein said heterologous protein consists of an α antigen from *M. kansasii*, into which the amino acid sequence Glu-Leu-Asp-Arg-Trp-Glu-Lys-Ile is inserted between 279-Gln and 280-Ala of said α antigen.

* * * * *